(12) United States Patent
Kreindel

(10) Patent No.: US 11,779,388 B2
(45) Date of Patent: Oct. 10, 2023

(54) RF FRACTIONAL DEVICE FOR TREATMENT AT DIFFERENT TISSUE DEPTHS

(71) Applicant: Inmode Ltd., Yokneam (IL)

(72) Inventor: Michael Kreindel, Richmond Hill (CA)

(73) Assignee: Inmode Ltd., Yokneam (IL)

( * ) Notice: Subject to any disclaimer, the term of this patent is extended or adjusted under 35 U.S.C. 154(b) by 408 days.

(21) Appl. No.: 17/004,312

(22) Filed: Aug. 27, 2020

(65) Prior Publication Data

US 2020/0390492 A1 Dec. 17, 2020

Related U.S. Application Data

(63) Continuation-in-part of application No. 15/427,332, filed on Feb. 8, 2017, now abandoned.

(51) Int. Cl.
*A61B 18/14* (2006.01)
*A61B 18/16* (2006.01)
(Continued)

(52) U.S. Cl.
CPC .......... *A61B 18/1477* (2013.01); *A61B 18/16* (2013.01); *A61B 2017/0023* (2013.01); *A61B 2017/00154* (2013.01); *A61B 2018/00452* (2013.01); *A61B 2018/00464* (2013.01); *A61B 2018/00559* (2013.01); *A61B 2018/00577* (2013.01); *A61B 2018/00589* (2013.01); *A61B 2018/00702* (2013.01); *A61B 2018/00779* (2013.01); *A61B 2018/00827* (2013.01); *A61B 2018/00875* (2013.01);
(Continued)

(58) Field of Classification Search
CPC . A61B 18/1485; A61B 18/1477; A61B 18/16; A61B 2018/00184; A61B 2018/00577; A61B 2018/00589; A61B 2018/143; A61B 2018/1475; A61B 2018/00083; A61B 2018/0016; A61B 2018/00327; A61B 2018/00559; A61B 2018/1425; A61B 2018/1467; A61B 2018/00107; A61B 2018/00452; A61B 2018/00464; A61B 2018/0047; A61B 2018/00702; A61B 2018/00779; A61B 2018/00827; A61B 2018/00875; A61B 2018/00892; A61B 2018/1253; A61B 2017/00154; A61B 2017/0023
See application file for complete search history.

(56) References Cited

U.S. PATENT DOCUMENTS

| | | | | |
|---|---|---|---|---|
| 2002/0120261 A1* | 8/2002 | Morris | ............... | A61M 25/1002 606/41 |
| 2004/0162551 A1* | 8/2004 | Brown | ...................... | A61N 1/40 606/41 |
| 2010/0222677 A1* | 9/2010 | Placek | ............... | A61B 18/1477 606/41 |

* cited by examiner

*Primary Examiner* — Khadijeh A Vahdat
(74) *Attorney, Agent, or Firm* — Dekel Patent Ltd.; David Klein

(57) ABSTRACT

A method of applying RF energy includes using an RF energy applicator assembly to apply RF energy to a tissue. The RF energy applicator assembly includes a housing, and RF electrodes coupled to an RF energy source and movably mounted in the housing. The RF electrodes have a retracted position, in which the RF electrodes are retracted inside the housing, and deployed positions in which the RF electrodes protrude out of the housing at different protrusion lengths. An actuator is coupled to the RF electrodes and configured to move the RF electrodes from the retracted position to any one of the deployed positions.

13 Claims, 4 Drawing Sheets

(51) Int. Cl.
- *A61B 18/00* (2006.01)
- *A61B 17/00* (2006.01)
- *A61B 18/12* (2006.01)

(52) U.S. Cl.
CPC ............... *A61B 2018/00892* (2013.01); *A61B 2018/1253* (2013.01); *A61B 2018/143* (2013.01); *A61B 2018/1467* (2013.01); *A61B 2018/1475* (2013.01)

RF FRACTIONAL DEVICE FOR TREATMENT AT DIFFERENT TISSUE DEPTHS

FIELD OF THE INVENTION

The invention relates to a device in the field of fractional treatment, such as but not limited to, for restoring shape and enhancing functionality of body related to the natural opening structure, and particularly to such treatments at different depths in the tissue.

BACKGROUND OF THE INVENTION

Fractional devices are known for skin treatment. Fractional injuries to the skin and dermis can be delivered by laser systems such as FRAXEL, which sends small beams of erbium glass laser wavelengths into the dermis or alternatively fractional devices as micro-needling, surface ablation or invasive needling. The advantage of these segmental, fractional injury, is the dermis is stimulated with an aggressive fractional trauma providing fractional skin resurfacing, skin tightening, acne scar and wrinkle treatment as well as treatment of hyperhydrosis, acne and trans dermal drug delivery.

U.S. Pat. No. 6,210,402 describes a method for dermatological treatment of an external body surface at applying high frequency electrical energy to the electrode terminal comprising multiple conductive elements.

U.S. Pat. Nos. 6,148,232 and 6,615,079 describe methods and devices for fractional ablation of stratum corneum for transdermal drug delivery.

U.S. Pat. Nos. 8,496,654 and 8,357,157 describe devices for cosmetic fractional epidermis ablation where multiple electrodes are applied to the skin surface and have a grounded return electrode.

U.S. Pat. No. 8,579,896 describes fractional coagulation of skin with electrodes configured not to penetrate into the skin.

U.S. Pat. No. 9,108,036 describes a skin treatment device including an applicator tip with a plurality of electrodes configured for contacting a stratum corneum layer for delivering RF energy.

U.S. Pat. No. 9,480,836 describes a needle array penetrating into the skin and powered by motor connecting to the array.

U.S. Pat. No. 9,233,241 describes an array of insertable needles and RF energy delivered to the needles.

The fractional RF treatment which was broadly used for skin treatment was totally ignored for medical applications required tissue remodeling inside the natural openings as vagina, anus, nose, ears, mouth and other assessable epithelial tissue.

SUMMARY OF THE INVENTION

The present invention is a procedure and method for delivery RF energy in fractional manner at different depths in tissues, such as but not limited to, natural openings and adjacent epithelial tissues. Wet environment inside the natural openings does not allow effective RF energy delivery by means of non-insertable electrodes because of significant RF leakage through the liquids. One example of the invention is an applicator configured to be inserted into the natural opening, which includes a mechanism for pushing an array of sharp electrodes through the surface of the epithelial tissue after the applicator is inserted into natural opening. An RF generator is configured for delivering RF energy to the array of electrode.

In some embodiments, such as for vaginal treatment, the applicator insertable part has a length of 3-15 cm and smooth surfaces for non-traumatic insertion. The array of electrodes can be designed as needles and the needle surfaces can be partially coated with non-conductive material for delivering more RF energy inside the tissue and less energy to the surface of the vagina and minimize leakage to the liquid presenting around the applicator.

The array of electrodes may include two or more conductive elements. The preferable design comprises a minimum of four elements for faster and effective treatment and not more than 25 needles to minimize force of needle insertion into the tissue. Conductive elements can be designed in the shape of needles, cones or pyramids. The length of conductive elements can vary from 0.1 mm up to 10 mm, depending on treatment requirements. The thickness or diameter of the conductive elements ranges from 0.1 mm up to 1 mm.

The distance between the conductive element and return electrodes may be at least 3 mm to be able to work in wet environments, such as in the presence of gel or natural liquids. Ideally the distance between electrodes with different polarity should be above 5 mm.

The applicator may have a disposable part for inserting into the opening and a non-disposable part that has more expensive mechanical and electronics elements. Alternatively, the entire applicator can be disposable if it is designed in an affordable way.

The non-disposable part may be a motor, solenoid or other electro-mechanical component that pushes or otherwise moves the array of electrodes (either directly or indirectly through linkage or intermediary components) toward the treated surface. The actuator may comprise one or more elements and may be electro-mechanical or mechanical, automatic, semi-automatic or manual. The mechanism may push the array of electrodes to the fixed distance or distances controlled by the user or a processor located inside the device. The distance that conductive elements protrude out of applicator is in the range of 0.1 mm up to 10 mm. The conductive elements can be pushed in radial, axial or any other direction required for the treatment. The direction of pushing can be fixed for specific application and alternatively it can be adjustable.

The mechanism may hide sharp parts of the conductive elements inside the applicator during moving the applicator inside the opening.

The applicator can be used for the treatment of outer body parts adjacent and distal from natural opening.

The RF generator generates alternating electrical voltage with frequency of 100 kHz to 40 MHz. The amount of RF energy should be high enough to coagulate and/or ablate the small amount of tissue around the conductive elements but not too high to prevent connection coagulation zones between the conductive elements. Minimizing the coagulated zones provides faster healing process. For more aggressive treatment the higher RF energy is applied.

The RF pulse power can be varied from 1 W to 500 W depending on the number of conductive elements. RF energy can be delivered with a train of short RF pulses having higher power. RF energy may be applied in a pulsed manner to minimize thermal zone. The pulse duration can be varied from 100 microseconds up to 500 milliseconds. With high RF power shorter pulses are required, whereas with low RF power a longer pulse width is needed to achieve the required thermal effect.

The RF energy can be applied between conductive elements in the array. Alternatively, RF voltage can be applied between conductive elements pushed into the tissue and side electrode or electrodes located on the applicator and having a larger area than the total area of conductive elements.

Alternatively, a mono-polar scheme can be used when a large area return electrode is placed on the skin surface.

The device powering the applicator may include a microprocessor for controlling the electronics and user interface. The microprocessor may monitor one or more from the following RF parameters including, but not limiting to, RF voltage, RF current, RF power, RF impedance, phase shift between RF voltage and RF current. In addition, the controller may control and monitor pushing and retraction of conductive elements.

BRIEF DESCRIPTION OF THE DRAWINGS

In the accompanying drawings:

FIG. 1b is a schematic depiction of one example of the applicator with radial direction of conductive elements retracted in.

DETAILED DESCRIPTION

Figure 1A:
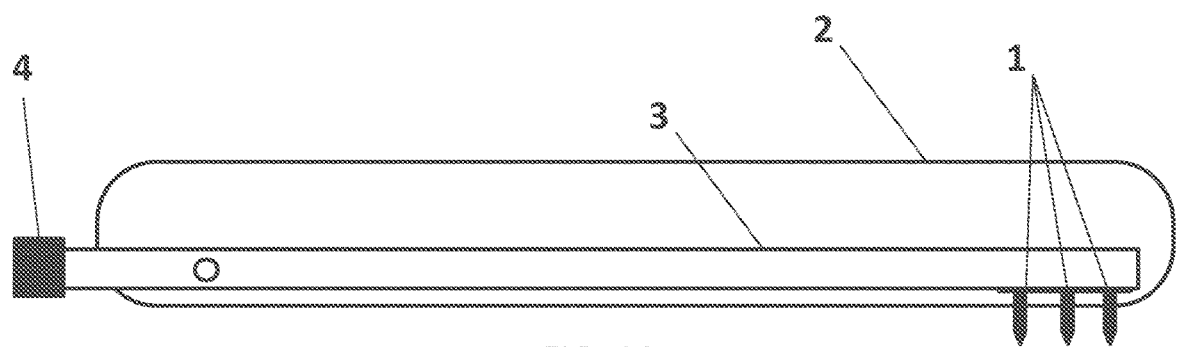
FIG. 1a is a schematic depiction of one example of an applicator with radial direction of conductive elements pushed out.
Figure 1B:
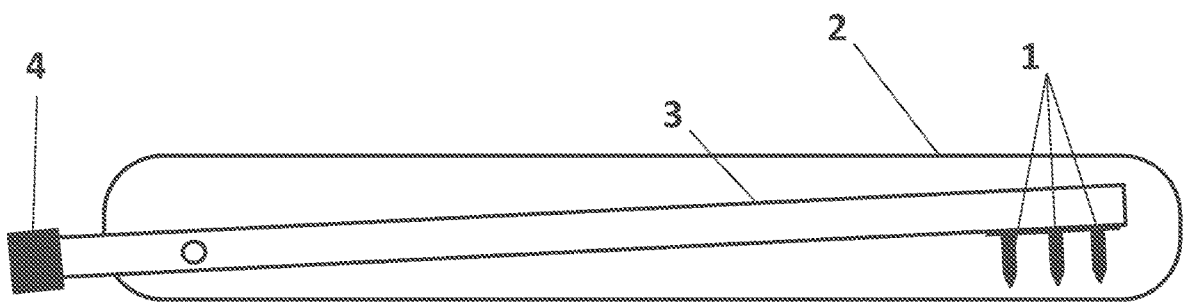

Referring first to FIGS. 1a and 1b, an applicator assembly includes a housing 2. An array of conductive elements 1 is directed radially and is coupled to a movable part 3 with a connector 4. By moving the movable part 3, the array of conductive elements may be retracted and hidden inside the applicator or deployed to protrude out of the applicator to penetrate the tissue surface.

FIG. 1a shows the applicator with conductive elements pushed outside of the applicator housing toward the treated tissue. FIG. 1b shows the applicator with conductive elements retracted into the applicator. RF current is delivered to the conductive elements through the connector 4 connecting to the RF generator.

Figure 2:
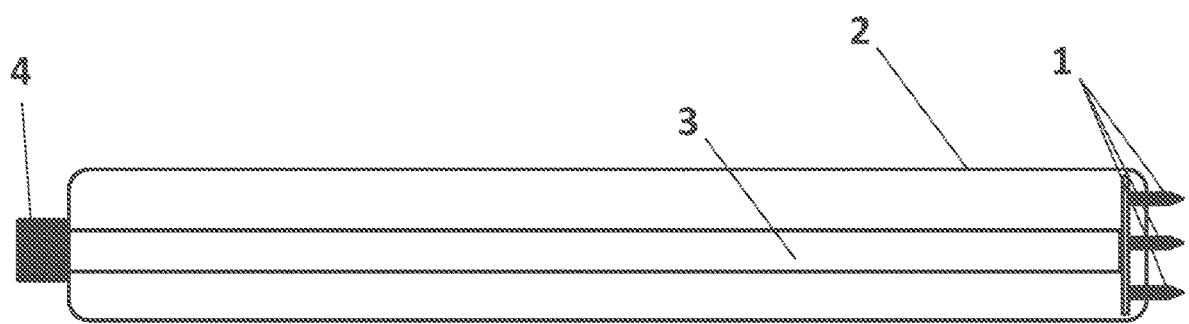
FIG. 2 is a schematic depiction of one example of an applicator with axial direction of conductive elements pushed out.

Referring to FIG. 2, an alternative applicator assembly has the array of conductive elements 1 directed axially. Array of conductive elements 1 is coupled to the movable part 3 with connector 4. By moving the movable part 3, the array of conductive elements may be retracted and hidden inside the applicator housing 2 or deployed to protrude out of the applicator to penetrate the tissue surface.

Figure 3:
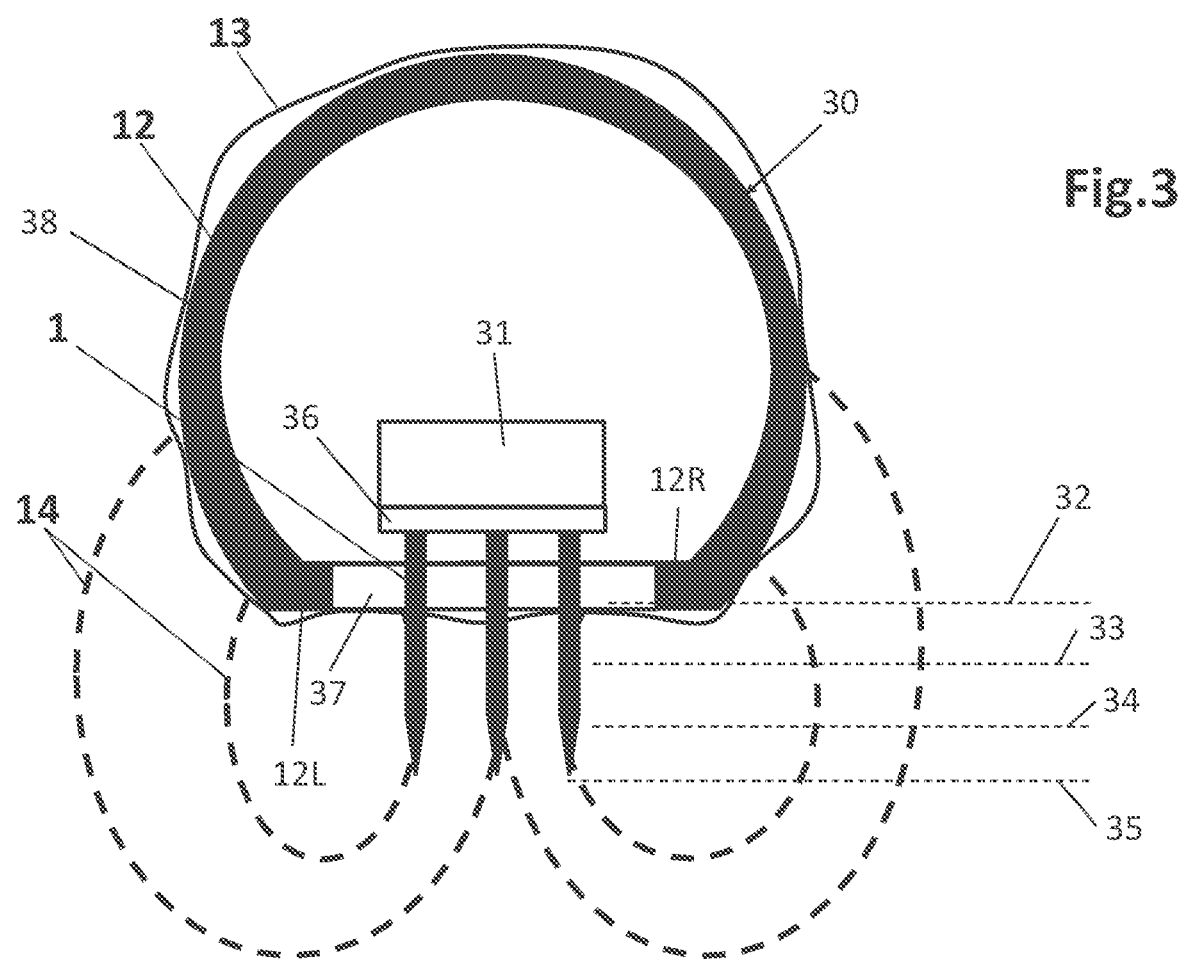
FIG. 3 is a schematic depiction of one example of RF current flowing between conductive elements and return electrode.

FIG. 3 shows schematically a cross-section of the assembly attached to the tissue 13. Array of conductive elements 1 shaped as needles penetrates the tissue and RF current 14 flows from conductive elements 1 to the return electrode 12 having a much larger area than the total area of the array of conductive elements 1. RF current 14 is concentrated on the sharp conductive elements 1 and creates a strong thermal effect in the vicinity of the needles while heating of tissue near the return electrode 12 is much less. RF energy is high enough to create desired thermal effects, such as coagulation or ablation of the tissue.

Figure 4:
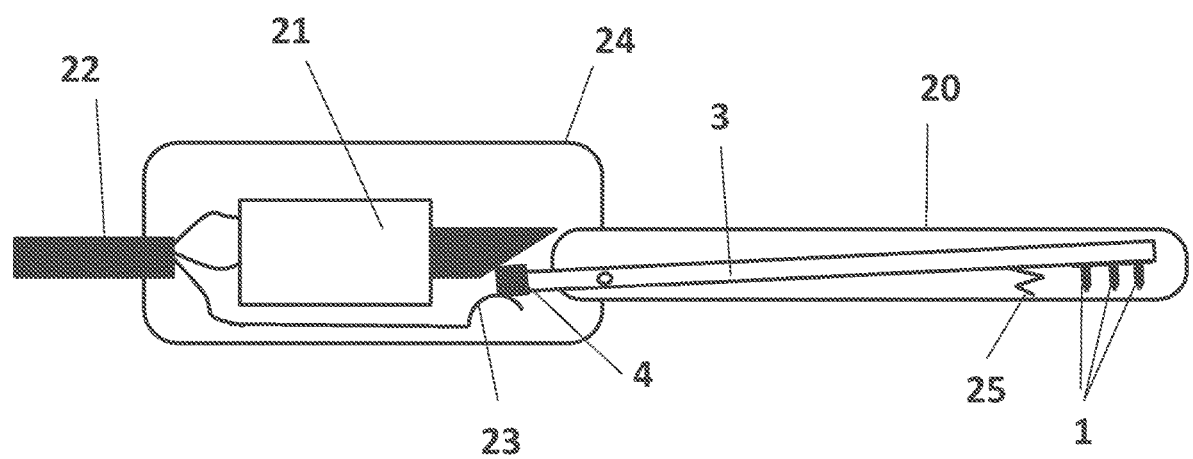
FIG. 4 is a schematic depiction of one example of an applicator attached to the handle.

FIG. 4 shows a disposable applicator 20 designed to contact the tissue of a patient and attached to a handle 24, which may be connected through a harness 22 to a controller (not shown). The handle 24 includes an electro-mechanical linear actuator 21 that causes movement of the movable part 3 in the disposable applicator to push the array of conductive elements 1 toward the tissue surface. When the linear actuator 21 is pulled back the spring 25 retracts conductive elements out of the tissue.

The preferred parameters for device are following:
1. Applicator length is from 10 mm to 200 mm
2. Applicator diameter (transverse dimension) is from 5 mm up to 40 mm.
3. Number of conductive elements can be up to 200 but preferably from 4 up to 25 for easier penetration into the tissue.
4. Time of pushing the array of conductive elements toward the tissue should be below 1 second.
5. The penetration depth of conductive elements is from 0.1 mm up to 10 mm. For some applications it can be predetermined while for others it should be adjustable.
6. RF voltage applied to the skin should be in the range of 10 V up to 1000 V.
7. Pulse repetition rate from 0.2 pps up 2 pps The tissue treated by the invention may be, without limitation, skin, fat, muscle or mucosal tissue or any combination thereof.

Any of the embodiments of the invention can be used to apply RF energy to tissue. The method includes using the RF energy applicator assembly to apply RF energy to a tissue. For example, in FIG. 3, the RF energy applicator assembly includes a housing 30, RF electrodes 1 coupled to an RF energy source 31 and movably mounted in the housing 30. The RF electrodes 1 have a retracted position (indicated by broken line 32), in which the RF electrodes 1 are retracted inside the housing 30, and deployed positions in which the RF electrodes 1 protrude out of the housing 30 at different protrusion lengths (indicated by broken lines 33, 34 and 35; the invention is not limited to this number of lengths). Actuator 36 is coupled to the RF electrodes 1 and configured to move the RF electrodes 1 from the retracted position to any one of the deployed positions.

In the method, the actuator 36 is used to move the RF electrodes 1 to one of the deployed positions so that the RF electrodes 1 penetrate into the tissue at a first depth, and the actuator 36 is used to move the RF electrodes 1 to a different one of the deployed positions so that the RF electrodes 1 penetrate into the tissue at a different depth. The RF energy is delivered to the tissue at some time while the RF electrodes 1 are located in the tissue. The RF electrodes 1 are retracted out of the tissue after application of a desired amount of RF energy to the tissue.

The RF energy may be delivered while the RF electrodes are or are not moving. The RF energy may be delivered at multiple depths. The RF energy may be delivered during insertion of the RF electrodes into the tissue or during retraction of the RF electrodes from the tissue.

The housing 30 includes a flat surface 37 that has left and right sides, and a curved outer shell 38 that extends from the left and the right sides. Return electrode 12 is in the curved outer shell 38. Return electrode 12 includes a left flat portion 12L that extends beyond the curved outer shell 38 through the left side into a portion of the flat surface 37, and a right flat portion 12R that extends beyond the curved outer shell 38 through the right side into another portion of the flat surface 37. The return electrode 12 is spaced from the RF electrodes 1.

The RF electrodes 1 may be mounted on a movable arm (like arm 3) disposed in the housing. The movable arm has a first position in which the RF electrodes are retracted inside the housing and multiple positions in which the RF electrodes protrude out of the flat surface of the housing at the deployed positions.

Accordingly, the RF energy may be delivered between movable electrodes or may be delivered between movable electrodes and a return electrode applied to a tissue surface.

The invention claimed is:

1. A method of applying radio frequency (RF) energy comprising:
    using an RF energy applicator assembly to apply RF energy to a tissue, said RF energy applicator assembly comprising a housing, RF electrodes coupled to an RF energy source and movably mounted in said housing, wherein said RF electrodes have a retracted position, in which said RF electrodes are retracted inside said housing, and deployed positions in which said RF electrodes protrude out of said housing at different protrusion lengths, and an actuator coupled to said RF electrodes and configured to move said RF electrodes from said retracted position to any one of said deployed positions;
    wherein said RF electrodes are mounted on a distal end of a movable arm disposed in said housing, said movable arm pivoting about a pivot which is proximal to said distal end, and wherein a biasing device is disposed distal to said pivot and biases said movable arm and said RF electrodes to said retracted position, and wherein said actuator is arranged to contact a proximal portion of said movable arm, proximal to said pivot, wherein movement of said actuator on said proximal portion causes said movable arm to pivot about said pivot and to move said RF electrodes to one of said deployed positions, and movement of said actuator in a different direction permits said biasing device to move said RF electrodes to said retracted position;
    using said actuator to move said RF electrodes to one of said deployed positions so that said RF electrodes penetrate into said tissue at a first depth;
    using said actuator to move said RF electrodes to a different one of said deployed positions so that said RF electrodes penetrate into said tissue at a different depth;
    delivering RF energy to said tissue at some time while said RF electrodes are located in said tissue; and
    retracting said RF electrodes out of said tissue after application of a desired amount of RF energy to said tissue.

2. The method according to claim 1, comprising delivering the RF energy while said RF electrodes are not moving.

3. The method according to claim 1, comprising delivering the RF energy while said RF electrodes are moving.

4. The method according to claim 1, comprising delivering the RF energy at multiple depths.

5. The method according to claim 1, comprising delivering the RF energy during insertion of said RF electrodes into said tissue.

6. The method according to claim 1, comprising delivering the RF energy during retraction of said RF electrodes from said tissue.

7. The method according to claim 1, wherein said tissue is skin, fat, muscle or mucosal tissue or any combination thereof.

8. The method according to claim 1, comprising delivering the RF energy between movable electrodes.

9. The method according to claim 1, comprising delivering the RF energy between movable electrodes and a return electrode applied to a tissue surface.

10. A radio frequency (RF) energy applicator assembly comprising:
    a housing;
    RF electrodes coupled to an RF energy source and movably mounted in said housing, wherein said RF electrodes have a retracted position, in which said RF electrodes are retracted inside said housing, and deployed positions in which said RF electrodes protrude out of said housing at different protrusion lengths; and
    an actuator coupled to said RF electrodes and configured to move said RF electrodes from said retracted position to any one of said deployed positions; and
    wherein said RF electrodes are mounted on a distal end of a movable arm disposed in said housing, said movable arm pivoting about a pivot which is proximal to said distal end, and wherein a biasing device is disposed distal to said pivot and biases said movable arm and said RF electrodes to said retracted position, and wherein said actuator is arranged to contact a proximal portion of said movable arm, proximal to said pivot, wherein movement of said actuator on said proximal portion causes said movable arm to pivot about said pivot and to move said RF electrodes to one of said deployed positions, and movement of said actuator in a different direction permits said biasing device to move said RF electrodes to said retracted position.

11. The RF energy applicator assembly according to claim 10, wherein said housing comprises a flat surface that has left and right sides, and a curved outer shell that extends from said left and said right sides, and a return electrode in said curved outer shell, said return electrode comprising a left flat portion that extends beyond said curved outer shell through said left side into a portion of said flat surface and a right flat portion that extends beyond said curved outer shell through said right side into another portion of said flat surface, said return electrode being spaced from said RF electrodes.

12. The RF energy applicator assembly according to claim 10, wherein said biasing device is proximal to said RF electrodes.

13. The RF energy applicator assembly according to claim 10, wherein said RF electrodes comprise sharp needles.

* * * * *